United States Patent
Hsu et al.

(10) Patent No.: US 11,517,276 B2
(45) Date of Patent: Dec. 6, 2022

(54) SCANNING IMAGING DEVICE, CARRIER AND CARRIER POSITIONING DEVICE

(71) Applicant: Delta Electronics, Inc., Taoyuan (TW)

(72) Inventors: Chih-Yuan Hsu, Taoyuan (TW); Yi-Da Tsai, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 1570 days.

(21) Appl. No.: 15/628,628

(22) Filed: Jun. 20, 2017

(65) Prior Publication Data
US 2018/0177471 A1    Jun. 28, 2018

(30) Foreign Application Priority Data
Dec. 27, 2016   (CN) .......................... 201611227712.2

(51) Int. Cl.
*F16M 11/00* (2006.01)
*A61B 6/00* (2006.01)
(Continued)

(52) U.S. Cl.
CPC .......... *A61B 6/4417* (2013.01); *A61B 5/0035* (2013.01); *A61B 5/055* (2013.01); *A61B 6/037* (2013.01); *A61B 6/4266* (2013.01); *A61B 6/508* (2013.01); *A61B 6/5247* (2013.01); *G01N 23/046* (2013.01); *G01R 33/481* (2013.01);
(Continued)

(58) Field of Classification Search
CPC ....... A61B 5/0035; A61B 5/055; A61B 6/037; A61B 6/4266; A61B 6/508; A61B 6/4417; G01N 23/046; G01R 33/046; G01R 33/4812
See application file for complete search history.

(56) References Cited

U.S. PATENT DOCUMENTS

| 2,209,477 | A  | * | 7/1940 | Reibel  | H02K 5/24  |
|           |    |   |        |         | 74/513     |
| 6,729,598 | B2 | * | 5/2004 | Folliot | B60N 2/0232 |
|           |    |   |        |         | 248/674    |
| 7,918,204 | B2 | * | 4/2011 | Gignac  | B01D 35/30  |
|           |    |   |        |         | 123/195 A  |

(Continued)

FOREIGN PATENT DOCUMENTS

| CN | 205379384 U | 7/2016 |
| JP | H03231642 A | 10/1991 |
| KR | 20100072873 A | 7/2010 |

OTHER PUBLICATIONS

Office Action dated Jun. 7, 2017 of the corresponding Taiwan patent application.

(Continued)

*Primary Examiner* — Amy J. Sterling
(74) *Attorney, Agent, or Firm* — Chun-Ming Shih; HDLS IPR Services (57) ABSTRACT

A carrier positioning device includes a carrying base (100) and a carrier (200). A clamp (110) is arranged on the carrying base (100) and a protruding hook (113) protrudes from one side of a distal end (111) of the clamp (110). The carrier (200) has a pipe (210), and a joint (220) is disposed at one end of the pipe (210). The protruding hook (113) hooks one side of the joint (220) so that at least another portion of the carrier (200) is in contact with the carrying base (100). Accordingly, the carrier (200) can be quickly installed or be removed along a lateral direction.

20 Claims, 9 Drawing Sheets

(51) Int. Cl.
  *A61B 5/00* (2006.01)
  *G01N 23/046* (2018.01)
  *A61B 5/055* (2006.01)
  *A61B 6/03* (2006.01)
  *G01R 33/48* (2006.01)
  *A61B 6/04* (2006.01)

(52) U.S. Cl.
  CPC ........ *G01R 33/4812* (2013.01); *A61B 5/0033* (2013.01); *A61B 6/03* (2013.01); *A61B 6/04* (2013.01); *A61B 6/0407* (2013.01)

(56) References Cited

U.S. PATENT DOCUMENTS

| | | |
|---|---|---|
| 10,886,813 B2 * | 1/2021 | Gonçalves Da Rosa .................... H02K 5/1732 |
| 2001/0052168 A1 | 12/2001 | Haase et al. |
| 2011/0092807 A1 | 4/2011 | Chiodo |
| 2014/0364722 A1 | 12/2014 | Dumoulin |

OTHER PUBLICATIONS

Search Report dated Jan. 31, 2018 of the corresponding European patent application No. EP17177587.7.
Office Action dated Sep. 23, 2020 of the corresponding China patent application No. 201611227712.2.

* cited by examiner

SCANNING IMAGING DEVICE, CARRIER AND CARRIER POSITIONING DEVICE

TECHNICAL FIELD

The present invention relates to a scanning imaging device and, in particular, to a scanning imaging device allowing a carrier thereof to be installed or removed along a lateral direction.

BACKGROUND

At present, in scanning imaging devices like an X-ray device, a computed tomography (CT) scanner, a magnetic resonance imaging (MRI) scanner, or a positron emission tomography (PET) scanner, usually a carrier thereof is axially installed to a machine table for easy positioning of the carrier. A scanned object placed in the carrier can be a living organism or a tissue. The carrier is typically arranged in a horizontal position, and the mechanism in the scanning imaging device moves coaxially and horizontally. The above-mentioned axial installment method needs to a large operation space around the machine table for installing the carrier. Since the mechanism in the scanning imaging device moves coaxially and horizontally, a cover plate or a through hole for operations is normally disposed laterally. As a result, the above-mentioned axial installment/removal method is considerably hampered by an outer housing or an outer cover, and thus it is inconvenient to operate the device.

Accordingly, the target of the inventor is to solve the above-mentioned problems, on the basis of which the present invention is accomplished.

SUMMARY

The present invention provides a scanning imaging device, a carrier and a carrier positioning device. The carrier of the scanning imaging device can be installed or removed quickly along a lateral direction by means of the carrier positioning device.

The present invention provides a carrier positioning device. The carrier positioning device includes a carrying base and a carrier. A clamp is disposed on the carrying base, and a protruding hook protrudes from one side of a distal end of the clamp. The carrier includes a pipe, a joint is disposed at one end of the pipe. The protruding hook hooks one side of the joint, so that at least another portion of the carrier is in contact with the carrying base.

In the carrier positioning device, the clamp is pivotally disposed in the carrying base, and the clamp is disposed with a resilient restoring element. The resilient restoring element is fixed inside the carrying base. The resilient restoring element pushes the clamp to pivotally rotate the clamp to be perpendicular to the carrying base. The joint includes a fastening groove, and the protruding hook hooks an inner edge of the fastening groove. A positioning plate is fixed to one side of the joint, the positioning plate is arranged horizontally at the carrying base, and the protruding hook hooks the positioning plate. An outer edge or a recessed portion of the positioning plate constitutes a portion of the inner edge of the fastening groove. The outer edge or the recessed portion of the positioning plate includes a slope facing away from the joint. A release button is pivotally disposed in the fastening groove, the release button is in contact with the protruding hook, and a resilient restoring element is fixed inside the joint and is connected between the release button and the joint. A middle section of the release button is pivotally fixed to the joint, and when the protruding hook is in contact with one end of the release button, the other end of the release button protrudes beyond a surface of the joint. When the release button pivotally rotates to push the protruding hook, the clamp is thereby pivotally rotated, and at the same time the protruding hook is disengaged away from the carrier. A slope is formed on the distal end of the clamp and is at the same side with the protruding hook. A positioning pin is vertically disposed on the carrying base, a positioning hole for insertion of the positioning pin is disposed at a side surface of the joint, and a tapered hole widening outwardly is formed at an outer end of the positioning hole. The carrying base includes a recess disposed corresponding to the joint for receiving the joint, a middle section of the clamp is pivotally fixed to the carrying base, and the distal end of the clamp protrudes in the recess, and a root portion of the clamp extends into the carrying base.

The present invention provides a scanning imaging device. The scanning imaging device includes a machine table, and the carrier positioning device is disposed in the machine table.

According to the present invention, the machine table of the scanning imaging device includes a slide rail, the slide rail is arranged horizontally, and the carrying base is disposed on the slide rail and is movable along the slide rail to move the carrier into the machine table horizontally. The machine table includes a through hole, a protruding base extends outwardly from the through hole, and the slide rail is disposed on the protruding base and extends into the through hole. The carrying base includes a recess disposed corresponding to the joint for receiving the joint, and the recess is open in a direction substantially perpendicular to an opening direction of the through hole of the machine table.

The present invention provides a carrier for a scanning imaging device. The carrier includes a pipe, a joint is disposed at one end of the pipe, the joint includes a fastening groove, a release button is pivotally disposed in the fastening groove, and a resilient restoring element is fixed inside the joint and is connected between the release button and the joint.

In the scanning imaging device of the present invention, a positioning plate is fixed to one side of the joint, and an outer edge or a recessed portion of the positioning plate constitutes a portion of an inner edge of the fastening groove. An outer edge or the recessed portion of the positioning plate includes a slope facing away from the joint.

According to the scanning imaging device and the carrier of the present invention, the carrier can be quickly installed or removed along a lateral direction by means of the carrier positioning device having the clamp collaborating with the joint of the carrier.

BRIEF DESCRIPTION OF THE DRAWINGS

The disclosure will become more fully understood from the detailed description, and the drawings given herein below is for illustration only, and thus does not limit the disclosure, wherein.

DETAILED DESCRIPTION

Figure 1:
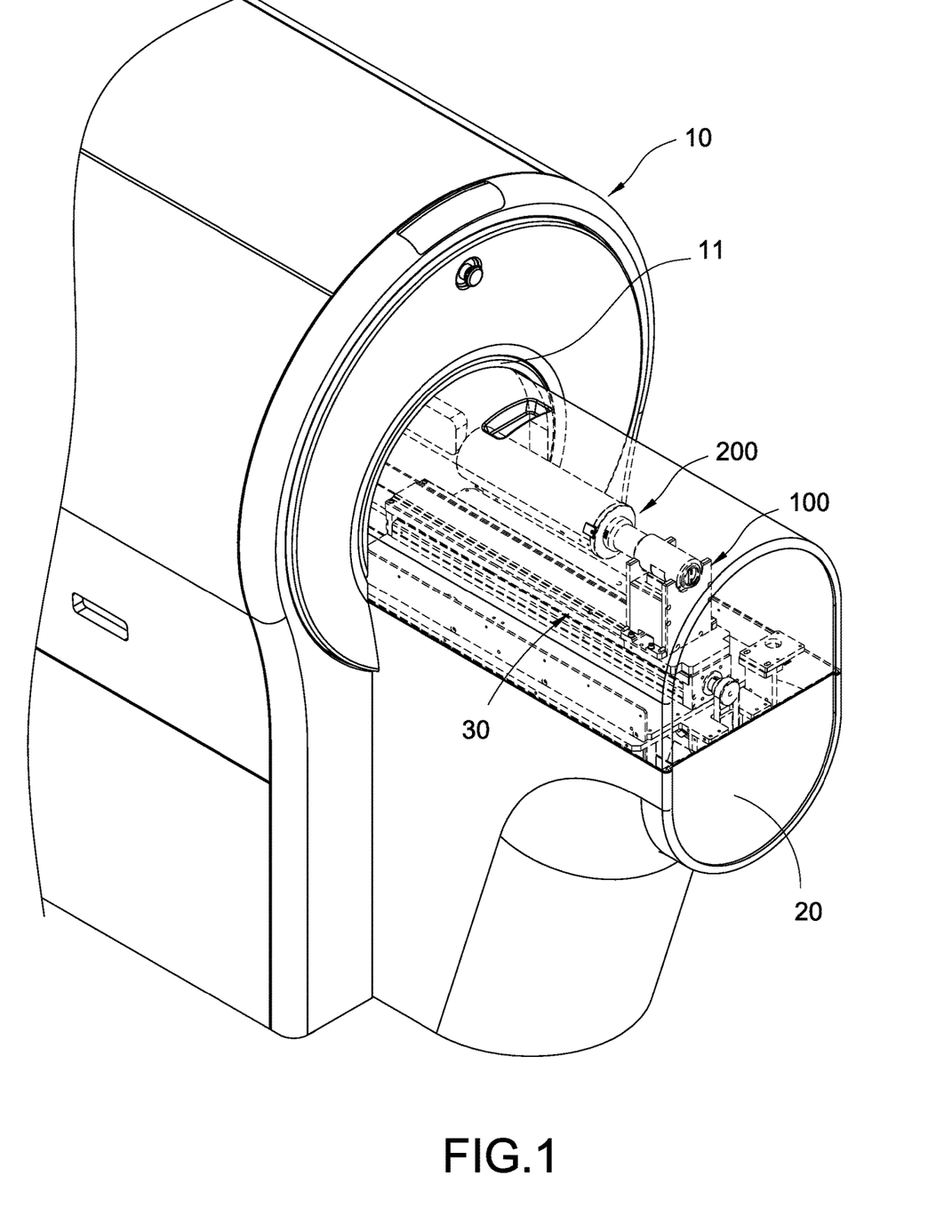
FIG. 1 is a perspective view illustrating a scanning imaging device according to one embodiment of the present invention.
Figure 2:
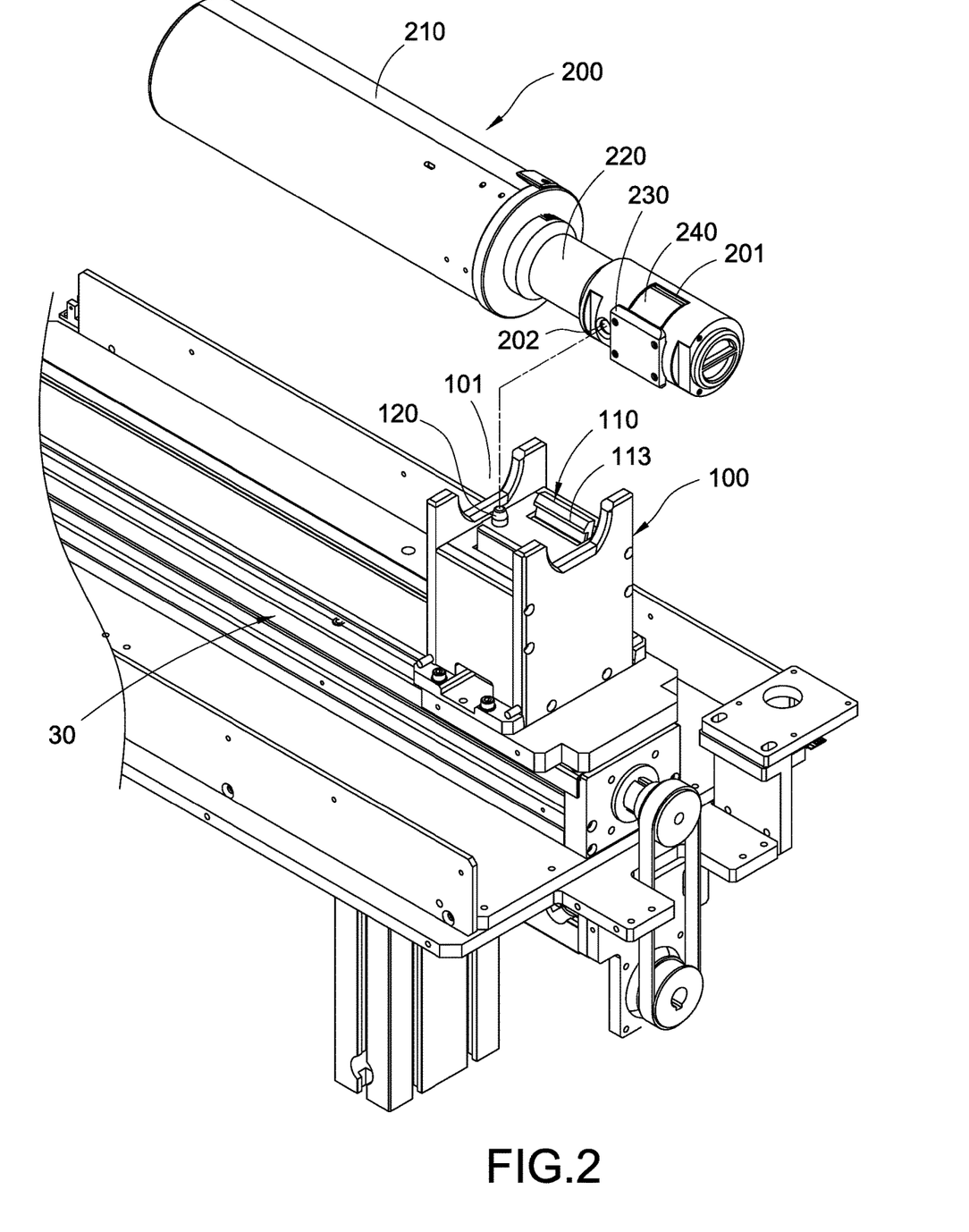
FIG. 2 is a perspective view showing configuration of the scanning imaging device according to one embodiment of the present invention.

Please refer to FIGS. 1 and 2, showing a scanning imaging device according to one embodiment of the present invention. The scanning imaging device includes a machine table 10 and a carrier 200.

A scanning device (not illustrated) is placed inside the machine table 10, so as to provide a scanned area in the machine table 10. The scanning device is, for example, an X-ray device, a computed tomography (CT) scanner, a magnetic resonance imaging (MRI) scanner, or a positron emission tomography (PET) scanner; however, the present invention is not limited in this regard.

The machine table 10 includes a through hole 11 and a protruding base 20 extending outwardly and axially from a bottom of the through hole 11. A slide rail 30 is disposed on the protruding base 20, the slide rail 30 is arranged horizontally along an opening direction of the through hole 11 and extends into the through hole 11, the carrying base 100 is disposed on the slide rail 30, and the carrying base 100 and the carrier 200 constitute a carrier positioning device. In the present embodiment, the carrying base 100 is preferably a hollow base, and the carrying base 100 is movable along the slide rail 30 to move toward or away from the through hole 11.

Figure 3:
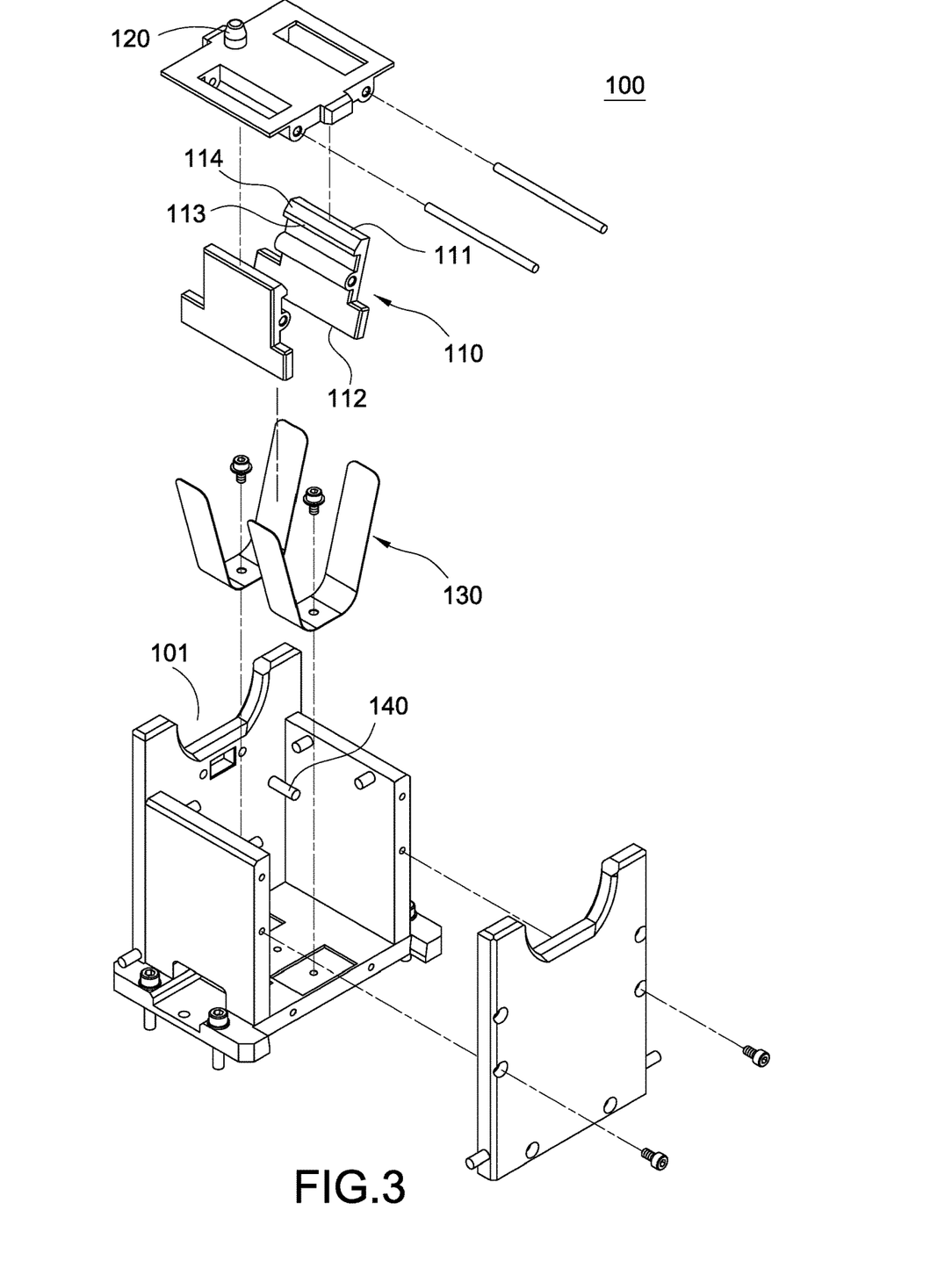
FIGS. 3 and 4 are perspective exploded view showing the scanning imaging device according to one embodiment of the present invention.

Referring to FIGS. 2 and 3, a top of the carrying base 100 includes a recess 101, and the recess 101 is open in a direction substantially perpendicular to the opening direction of the through hole 11 of the machine table 10. At least one clamp 110 is disposed on the carrying base 10. In the present embodiment, there are preferably two clamps 110, with the same structure and functions, vertically disposed on the carrying base 100; however, present invention is not limited to any specific number of the clamps 110. Two ends of each clamp 110 are a distal end 111 and a root portion 112. A middle section of the clamp 110 is pivotally fixed to the carrying base 100. The distal end 111 of the clamp 110 extends upwards and vertically protrudes out of the carrying base 100. The root portion 112 of the clamp 110 extends to the inside of the carrying base 100. A protruding hook 113 protrudes from one side of the distal end 111 of each clamp 110. The two protruding hooks 113 are disposed corresponding to each other and are disposed in the recess 101. A slope 114 is formed on the distal end 111 of each clamp 110 and is at the same side with the protruding hook 113. A positioning pin 120 vertically protrudes from the top of the carrying base 100. Each clamp 110 is disposed with a resilient restoring element 130. In the present embodiment, each resilient restoring element 130 is preferably a resilient arm fixed inside the carrying base 100. However, the resilient restoring element 130 can also be, for example, a pneumatic cylinder or a hydraulic cylinder, and the present invention is not limited to any specific form of the resilient restoring element 130. One end of each resilient restoring element 130 is fixed to an inner surface of the carrying base 100. In some embodiments, the ends of two resilient restoring elements 130 fixed to the inner surface of the carrying base 100 are connected with each other as one piece. The other end of each resilient restoring element 130 is in contact with the root portion 112 of the corresponding clamp 110. A restriction pillar 140 is disposed corresponding to each clamp 110 in the carrying base 100. In the present embodiment, the restriction pillar 140 serves to block the root portion 112 of each clamp 110 to restrict an initial position of the clamp 110 in its pivoting route. When the root portion 112 of the clamp 110 is in contact with the positioning pillar 140, the clamp 110 is vertically disposed at the top of the carrying base 100, and each resilient restoring element 130 pushes the root portion 112 of the clamp 110 to the corresponding restriction pillar 140.

Figure 4:
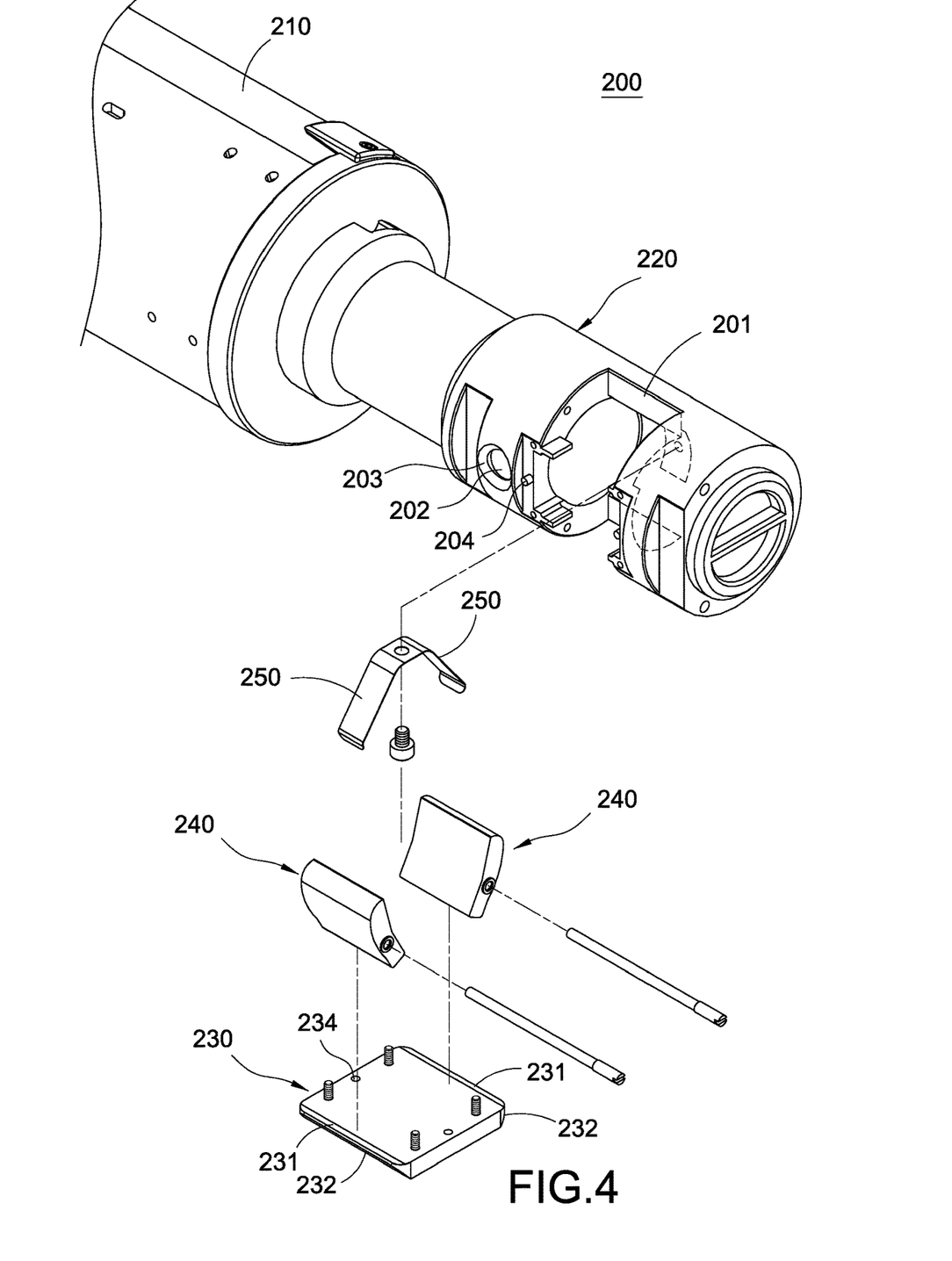

Referring to FIGS. 2 and 4, the carrier 200 includes a pipe 210 and a joint 220. The pipe 210 is adapted to receive a living organism or a tissue. The joint 220 is disposed at one end of the pipe 210. In the present embodiment, the joint 220 is preferably in a round-tube shape, and the joint 220 and the pipe 210 are coaxially connected or are fastened to each other to form one unit.

A side surface of the joint 220 includes a fastening groove 201. In the present embodiment, there are two fastening grooves 201 at two opposite sides on the joint 220, corresponding to the clamps 110. The protruding hook 113 hooks an inner edge of the fastening groove 201 at the side surface of the joint 220, so that the carrier 200 is fixed to the carrying base 100. A positioning plate 230 is selectively fixed to one side of the joint 220. In the present embodiment, the positioning plate 230 is disposed between the two fastening grooves 201; the positioning plate 230 is a rectangular plate and includes two outer edges 231 opposite to each other. Each outer edge 231 of the positioning plate 230 constitutes a portion of the inner edge of each fastening groove 201. The outer edge 231 of the positioning plate 230 includes a slope 232 facing away from the joint 220. In other embodiments, the positioning plate 230 can include two recessed portions (not illustrated) to constitute a portion of the inner edge of each fastening groove 201. A side edge of the recessed portion includes a slope (not illustrated) facing away from the joint 220. A positioning hole 202 for insertion of the positioning pin 120 is disposed at the side surface of the joint 220, and a tapered hole 203 widening outwardly is formed at an outer end of the positioning hole 202. In the present embodiment, a positioning hole 202 is open in a direction perpendicular to the positioning plate 230. The positioning hole 202 can be interchanged with the positioning pin 120.

A release button 240 is pivotally disposed in the fastening groove 201. In the present embodiment, each release button 240 is of elongated shape, each release button 240 is disposed in the corresponding fastening groove 201 to cover the same, and a middle section of each release button 240 is pivotally fixed to the inner edge of the fastening groove 201. One end of each release button 240 is adjacent to a corresponding one of the two outer edges 231 of the positioning plate 230. A resilient restoring element 250 is connected between each release button 240 and the joint 220. In the present embodiment, each resilient restoring element 250 is preferably a resilient arm fixed in the joint 220; however, the present invention is not limited in this regard, and each resilient restoring element 250 can also be, for example, a pneumatic cylinder or a hydraulic cylinder. One end of each resilient restoring element 250 is fixed to the inner surface of the joint 220. In some embodiments, the ends of two resilient restoring elements 250 fixed to the inner surface of the joint 220 are connected with each other as one piece. The other end of each resilient restoring element 250 is in contact with the other end of the corresponding release button 240.

Figure 5:
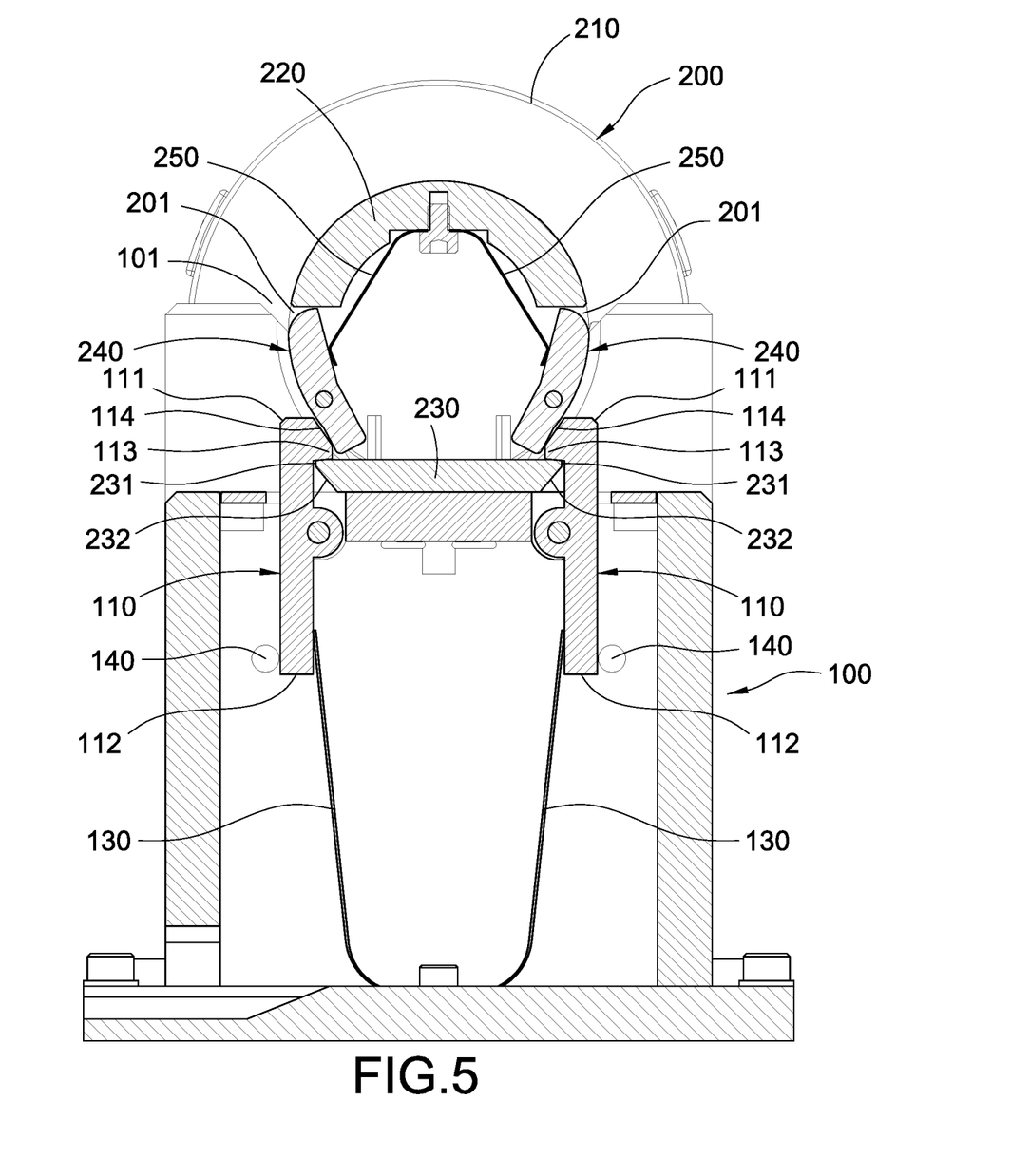
FIGS. 5 to 7 are schematic in-use views showing the scanning imaging device according to one embodiment of the present invention.

Referring to FIG. 5, when it is desired to use the scanning imaging device, the carrier 200 has to be installed horizontally or axially on the carrying base 100, and then the carrier 200 is moved, with the carrying base 10 moving along the slide rail 30, into a scanning imaging area inside the machine table 10 via the through hole 11 for scanning operations. The recess 101 on the carrying base 100 is configured to receive the joint 220 of the carrier 200. To install the carrier 200, the joint 220 is accurately joined to the positioning plate 230, then the joint 220 is horizontally placed in the recess 101, and the positioning pin 120 on the carrying base 100 is inserted into the positioning hole 202 on the joint 220 to position the carrier 200. The tapered hole 203 at the outer end of the positioning hole 202 can guide the positioning pin 120, so that the positioning pin 120 can be easily aligned with the positioning hole 202. The slope 114 at the distal end 111 of each clamp 110 contacts and pushes the slope 232 at the corresponding outer edge 231 of the positioning plate 230, so that the clamp 110 is pivotally rotated to make the protruding hook 113 thereof to move away to cross the outer edge 231. In the present embodiment, it is preferable that both the clamp 110 and the joint 220 include the slope 114 and 232 respectively. However, either the clamp 110 or the joint 220 is required to have the slope 114/232 in order to push the other one to pivotally rotate the clamp 110. When the protruding hook 113 crosses the outer edge 231, the resilient restoring element 130 disposed at the clamp 110 pushes the clamp 110 to make it pivotally rotate and return, so that the protruding hook 113 hooks the outer edge 231. As a result, each protruding hook 113 hooks the inner edge of the fastening groove 201 at the side surface of the joint 220, so as to fix the carrier 200 to the carrying base 100. In the present embodiment, the positioning plate 230 is used for horizontal positioning of the carrier 200. By the protruding hook 113 engaged with the positioning plate 230, the carrier 200 is positioned on the carrying base 100 more accurately. A portion of the inner edge of the fastening groove 201 enables accurate positioning of the carrier 200 by means of the positioning plate 230; however, the present invention does not require the positioning plate 230 as a requisite element for forming the inner edge of the fastening groove 201. The joint 220 and the positioning plate 230 each have a retaining structure 204/234, and the retaining structures 204, 234 are disposed corresponding to each other. In the present embodiment, the retaining structures 204, 234 are a pin and a hole engaged with each other, thereby facilitating positioning of the joint 220 and the positioning plate 230. At the same time, each protruding hook 113 contacts, in the fastening groove 201 where it is engaged, one end of the release button 240 adjacent to the positioning plate 230. Consequently, the other end of the release button 240 is pushed out of the surface of the joint 220 for being pressed.

According to one embodiment of the present invention, there are preferably two same clamps 110 for fixing the carrier 200; however, the present invention is not limited in this regard. That is to say, the carrier 200 can be fixed if one single protruding hook 113 hooks the joint 220, and at least another portion (e.g. another portion of the joint 220, the other fastening groove 201, or the positioning hole 202) of the carrier 200 contacts any place (e.g. the other protruding hook 113, the recess 101, or the positioning pin 120) of the carrying base 100.

Figure 6:
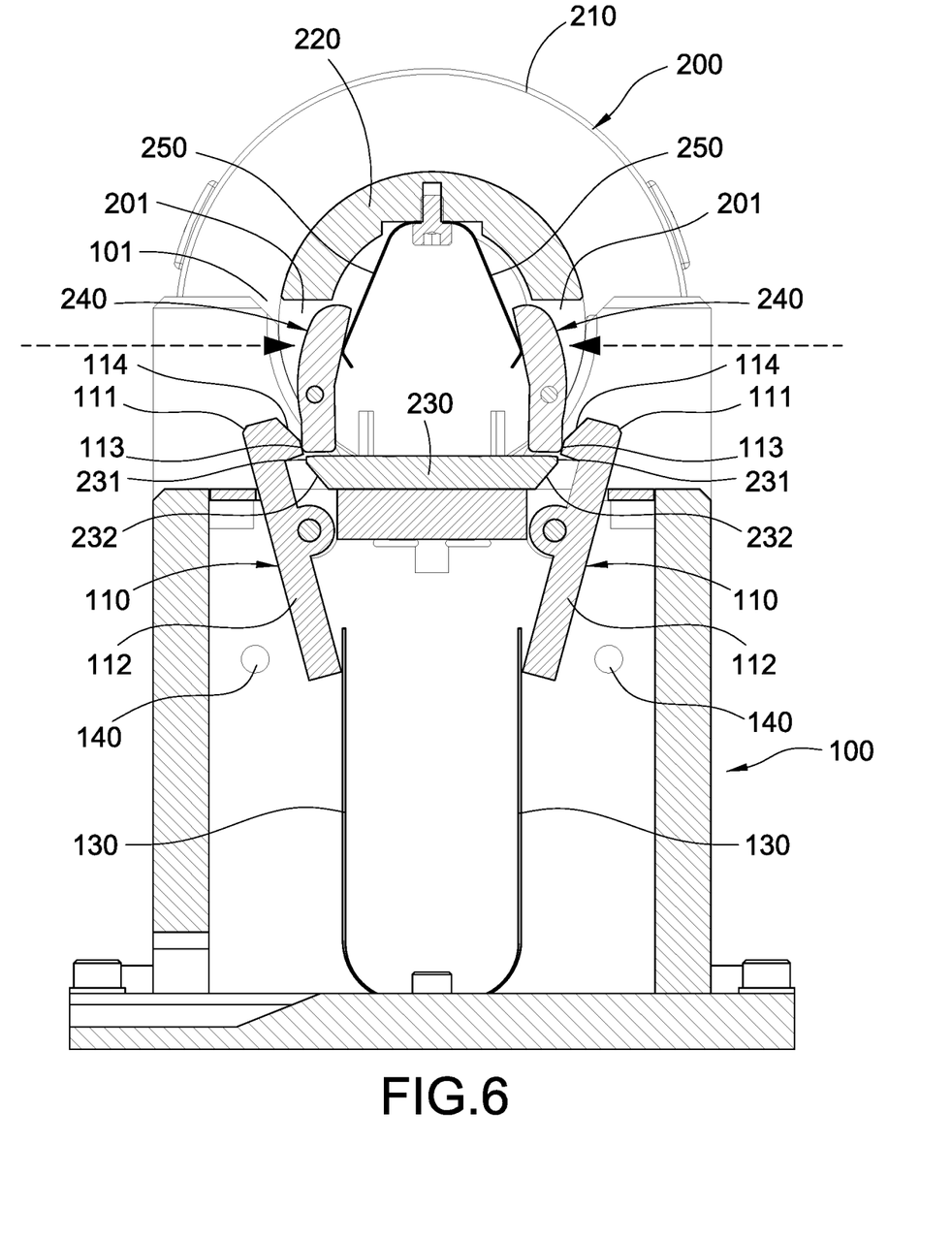
Figure 7:
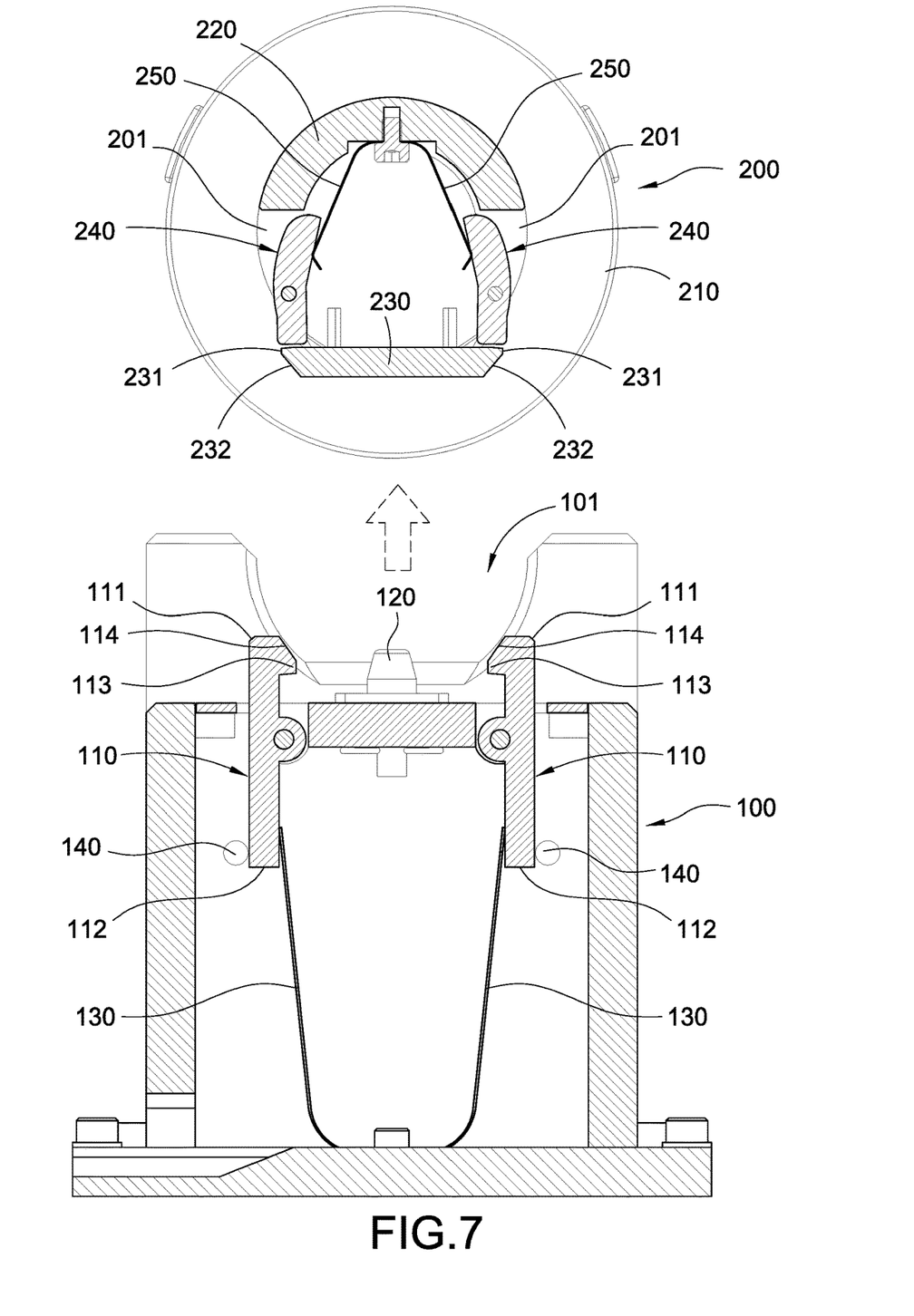

Referring to FIGS. 6 and 7, when it is desired to remove the carrier 200, a user can press the other end of each release button protruding out of the surface of the joint 220 while holding the carrier 200, so as to pivotally rotate each release button 240 to make the other end thereof to push each protruding hook 113 to thereby pivotally rotate each clamp 110, and thus each protruding hook 113 is disengaged away from the joint 220. Then, the carrier 200 can be removed. Accordingly, the carrier 200 can be removed in a direction substantially perpendicular to the opening direction of the through hole 11. When the user releases each release button 240, the resilient restoring element 250 connected thereto pushes each release button 240 to make it pivotally rotate and return.

Figure 8:
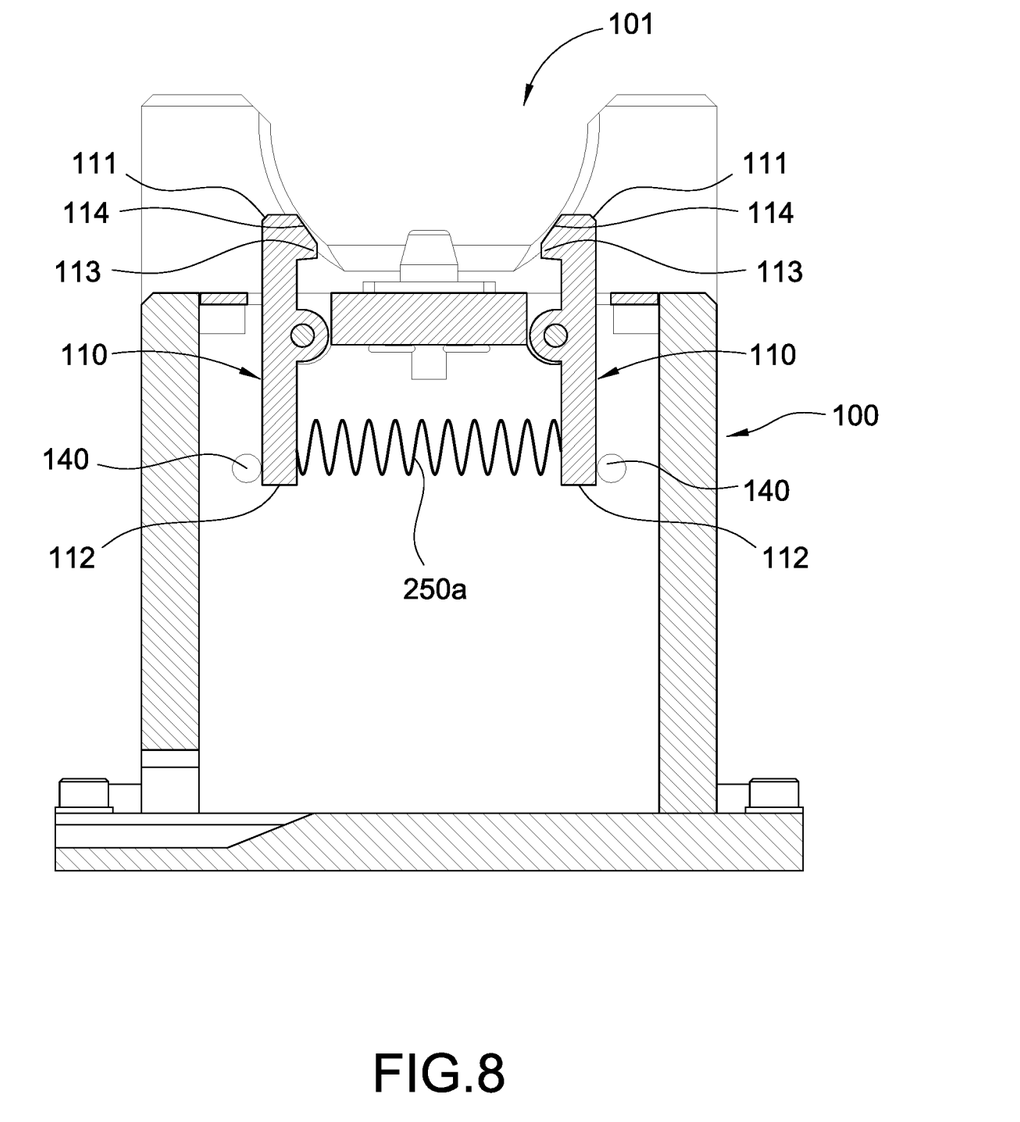
FIGS. 8 and 9 are schematic views showing a resilient restoring element of the scanning imaging device according to other embodiments of the present invention.
Figure 9:
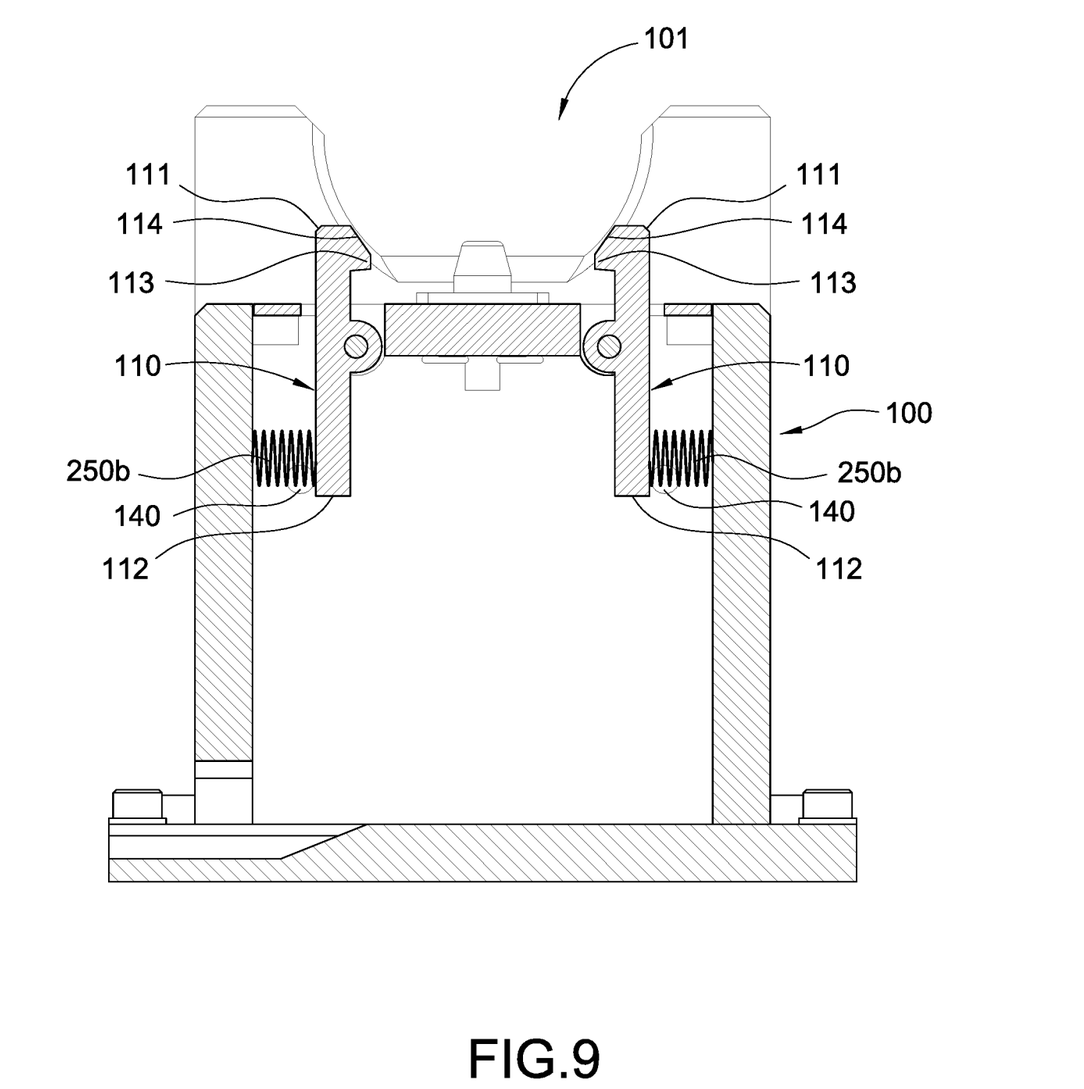

Referring to FIG. 8, according to another embodiment, the resilient restoring element 130 on the carrying base 100 can be a spring disposed between the root portions 112 of the two clamps 110. Two ends of the resilient restoring element 250a are in contact with the root portions 112 of the two clamps 110, respectively, so as to push the root portions 112 of the two clamps 110 to be away from each other, and thereby each clamp 110 is pivotally rotated to make each protruding hook 113 return. Referring to FIG. 9, the resilient restoring element 250b can also be disposed between the root portion 112 of each clamp 110 and the inner surface of the carrying base 100.

In the scanning imaging device of the present invention, the clamp 110 of the carrier positioning device collaborates with the joint 220 of the carrier 200, so that the carrier 200 can be quickly installed or removed along the lateral direction of the carrier 200 or the through hole 11. Therefore, it is easy and convenient to install or remove the carrier 200, and an operation space for installing or removing the carrier 200 laterally is over the through hole 11, so the machine table 100 does not require a large floor space. Furthermore, the carrier 200 can be accurately positioned in the scanning imaging device for better image quality.

It is to be understood that the above descriptions are merely the preferable embodiments of the present invention and are not intended to limit the scope of the present invention. Equivalent changes and modifications made in the spirit of the present invention are regarded as falling within the scope of the present invention.

What is claimed is:

1. A carrier positioning device, comprising:
a carrying base (100), a clamp (110) being disposed on the carrying base (100), a protruding hook (113) protruding from one side of a distal end (111) of the clamp (110); and
a carrier (200) including a pipe (210) and a joint (220) disposed at one end of the pipe (210), wherein the protruding hook (113) hooks one side of the joint (220) so that at least another portion of the carrier (200) is in contact with the carrying base (100),
wherein the clamp (110) is pivotally disposed in the carrying base (100), and the clamp (110) is disposed with a resilient restoring element (130).

2. The carrier positioning device of claim 1, wherein the resilient restoring element (130) is fixed inside the carrying base (100).

3. The carrier positioning device of claim 1, wherein the resilient restoring element (130) pushes the clamp (110) to pivotally rotate the clamp (110) to be perpendicular to the carrying base (100).

4. The carrier positioning device of claim 1, wherein the joint (220) includes a fastening groove (201), and the protruding hook (113) hooks an inner edge of the fastening groove (201).

5. The carrier positioning device of claim 4, wherein a positioning plate (230) is fixed to one side of the joint (220), the positioning plate (230) is arranged horizontally at the carrying base (100), and the protruding hook (113) hooks the positioning plate (230).

6. The carrier positioning device of claim 5, wherein an outer edge (231) or a recessed portion of the positioning plate (230) constitutes a portion of the inner edge of the fastening groove (201).

7. The carrier positioning device of claim 6, wherein the outer edge (231) or the recessed portion of the positioning plate (230) includes a slope (232) facing away from the joint (220).

8. The carrier positioning device of claim 4, wherein a release button (240) is pivotally disposed in the fastening groove (201), the release button (240) is in contact with the protruding hook (113), and a resilient restoring element (250/250a) is fixed inside the joint (220) and is connected between the release button (240) and the joint (220).

9. The carrier positioning device of claim 8, wherein a middle section of the release button (240) is pivotally fixed to the joint (220), and when the protruding hook (113) is in contact with one end of the release button (240), the other end of the release button (240) protrudes beyond a surface of the joint (220).

10. The carrier positioning device of claim 8, wherein when the release button (240) pivotally rotates to push the protruding hook (113), the clamp (110) is thereby pivotally rotated and at the same time the protruding hook (113) is disengaged away from the carrier (200).

11. The carrier positioning device of claim 1, wherein a slope (114) is formed on the distal end (111) of the clamp (110) and is at the same side with the protruding hook (113).

12. The carrier positioning device of claim 1, wherein a positioning pin (120) is vertically disposed on the carrying base (100), a positioning hole (202) for insertion of the positioning pin (120) is disposed at a side surface of the joint (220), and a tapered hole (203) widening outwardly is formed at an outer end of the positioning hole (202).

13. The carrier positioning device of claim 1, wherein the carrying base (100) includes a recess (101) disposed corresponding to the joint (220) for receiving the joint (220), a middle section of the clamp (110) is pivotally fixed to the carrying base (100), the distal end (111) of the clamp (110) protrudes in the recess (101), and a root portion (112) of the clamp (110) extends into the carrying base (100).

14. A scanning imaging device, comprising:
a machine table (10),
a carrier positioning device disposed in the machine table (10), the carrier positioning device comprising:
a carrying base (100), a clamp (110) being disposed on the carrying base (100), a protruding hook (113) protruding from one side of a distal end (111) of the clamp (110); and
a carrier (200) including a pipe (210) and a joint (220) disposed at one end of the pipe (210), wherein the protruding hook (113) hooks one side of the joint (220) so that at least another portion of the carrier (200) is in contact with the carrying base (100),
wherein the clamp (110) is pivotally disposed in the carrying base (100), and the clamp (110) is disposed with a resilient restoring element (130).

15. The scanning imaging device of claim 14, wherein the machine table (10) includes a slide rail (30), the slide rail (30) is arranged horizontally, and the carrying base (100) is disposed on the slide rail (30) and is movable along the slide rail (30) to move the carrier (200) into the machine table (10) horizontally.

16. The scanning imaging device of claim 15, wherein the machine table (10) includes a through hole (11), a protruding base (20) extends outwardly from the through hole (11), and the slide rail (30) is disposed on the protruding base (20) and extends into the through hole (11).

17. The scanning imaging device of claim 16, wherein the carrying base (100) includes a recess (101) disposed corresponding to the joint (220) for receiving the joint (220), and the recess (101) is open in a direction substantially perpendicular to an opening direction of the through hole (11) of the machine table (10).

18. A carrier (200) for a scanning imaging device, comprising a pipe (210), a joint (220) being disposed at one end of the pipe (210), the joint (220) including a fastening groove (201), a release button (240) being pivotally disposed in the fastening groove (201), a resilient restoring element (250/250a) being fixed inside the joint (220) and being connected between the release button (240) and the joint (220).

19. The carrier (200) of claim 18, wherein a positioning plate (230) is fixed to one side of the joint (220), and an outer edge (231) or a recessed portion of the positioning plate (230) constitutes a portion of an inner edge of the fastening groove (201).

20. The carrier (200) of claim 19, wherein an outer edge (231) or the recessed portion of the positioning plate (230) includes a slope (232) facing away from the joint (220).

* * * * *